US012723261B2

(12) United States Patent
Rao et al.

(10) Patent No.: US 12,723,261 B2
(45) Date of Patent: Sep. 1, 2026

(54) PROCESS FOR PRODUCING A PLURALITY OF NEDDYLATION SITE MODIFIED AAV2 VECTORS

(71) Applicants: INDIAN INSTITUTE OF TECHNOLOGY KANPUR, Kanpur (IN); Jayandharan Giridhara Rao, Kanpur (IN); Shubham Maurya, Kanpur (IN)

(72) Inventors: Jayandharan Giridhara Rao, Kanpur (IN); Shubham Maurya, Kanpur (IN)

(73) Assignees: INDIAN INSTITUTE OF TECHNOLOGY KANPUR, Kanpur (IN); Jayandharan Giridhara Rao, Kanpur (IN); Shubham Maurya, Kanpur (IN)

( * ) Notice: Subject to any disclaimer, the term of this patent is extended or adjusted under 35 U.S.C. 154(b) by 1231 days.

(21) Appl. No.: 17/294,222

(22) PCT Filed: Aug. 21, 2019

(86) PCT No.: PCT/IB2019/057036
§ 371 (c)(1),
(2) Date: May 14, 2021

(87) PCT Pub. No.: WO2020/058786
PCT Pub. Date: Mar. 26, 2020

(65) Prior Publication Data

US 2022/0307051 A1 Sep. 29, 2022

(30) Foreign Application Priority Data

Sep. 18, 2018 (IN) ............................. 201811035192

(51) Int. Cl.
*C12N 15/86* (2006.01)

(52) U.S. Cl.
CPC .... *C12N 15/86* (2013.01); *C12N 2750/14122* (2013.01); *C12N 2750/14143* (2013.01)

(58) Field of Classification Search
None
See application file for complete search history.

(56) References Cited

PUBLICATIONS

Yavuz et al., BMC Bioinformatics, Dec. 16, 2015(Suppl 18):S9. (Year: 2015).*

Yavuz et al.; “Prediction of neddylation sites from protein sequences and sequence-derived properties,” BMC Bioinformatics; Dec. 9, 2015.

Yuan et al., “SIRT 1 Regulates the Function of the Nijmegen Breakage Syndrome Protein” Molecular Cell; Jul. 6, 2007.

Hauswirth et al.; Treatment of leber congenital amaurosis due to RPE65 mutations by ocular subretinal injection of adeno-associated virus gene vector; Oct. 19, 2008.

* cited by examiner

*Primary Examiner* — Nicole Kinsey White
(74) *Attorney, Agent, or Firm* — Dickinson Wright PLLC

(57) ABSTRACT

The present invention provides a process for producing a plurality of Neddylation site modified AAV vectors. In one embodiment, the process comprises predicting a plurality of Neddylation sites on AAV VP1 capsid protein sequence based on relatively high confidence targets, wherein the AAV VP1 capsid protein sequence being set forth in Protein ID-YP_680426.1; and producing the plurality of Neddylation site modified AAV vectors based on predicted plurality of neddylation sites on AAV VP1 capsid protein sequence. The present invention for the first time highlights the role of Neddylation during AAV infection and its impact on generating novel AAV vectors with improved efficiency for ocular and hepatic gene therapy.

7 Claims, 14 Drawing Sheets

Specification includes a Sequence Listing.

Post 8 weeks imaging

SEQUENCE LISTING

```
<160> NUMBER OF SEQ ID NOS: 18

<210> SEQ ID NO 1
<211> LENGTH: 44
<212> TYPE: DNA
<213> ORGANISM: adeno-associated virus 2

<400> SEQUENCE: 1

aaacctggcc caccaccacc acagcccgca gagcggcata agga                        44


<210> SEQ ID NO 2
<211> LENGTH: 44
<212> TYPE: DNA
<213> ORGANISM: adeno-associated virus 2

<400> SEQUENCE: 2

tccttatgcc gctctgcggg ctgtggtggt ggtgggccag gttt                        44


<210> SEQ ID NO 3
<211> LENGTH: 33
<212> TYPE: DNA
<213> ORGANISM: adeno-associated virus 2

<400> SEQUENCE: 3

cttcaacgga ctcgaccagg gagagccggt caa                                    33


<210> SEQ ID NO 4
<211> LENGTH: 33
<212> TYPE: DNA
<213> ORGANISM: adeno-associated virus 2

<400> SEQUENCE: 4

ttgaccggct ctccctggtc gagtccgttg aag                                    33


<210> SEQ ID NO 5
<211> LENGTH: 39
<212> TYPE: DNA
<213> ORGANISM: adeno-associated virus 2
```

<400> SEQUENCE: 5
catgggtgga ttcggacttc aacaccctcc tccacagat 39

<210> SEQ ID NO 6
<211> LENGTH: 39
<212> TYPE: DNA
<213> ORGANISM: adeno-associated virus 2

<400> SEQUENCE: 6
atctgtggag gagggtgttg aagtccgaat ccacccatg 39

<210> SEQ ID NO 7
<211> LENGTH: 40
<212> TYPE: DNA
<213> ORGANISM: adeno-associated virus 2

<400> SEQUENCE: 7
ccagcagcga gtatcacaga catctgcgga taacaacaac 40

<210> SEQ ID NO 8
<211> LENGTH: 40
<212> TYPE: DNA
<213> ORGANISM: adeno-associated virus 2

<400> SEQUENCE: 8
gttgttgtta tccgcagatg tctgtgatac tcgctgctgg 40

<210> SEQ ID NO 9
<211> LENGTH: 33
<212> TYPE: DNA
<213> ORGANISM: adeno-associated virus 2

<400> SEQUENCE: 9
accaccttca gtgcggcaca gtttgcttcc ttc 33

<210> SEQ ID NO 10
<211> LENGTH: 33
<212> TYPE: DNA
<213> ORGANISM: adeno-associated virus 2

<400> SEQUENCE: 10
gaaggaagca aactgtgccg cactgaaggt ggt 33

<210> SEQ ID NO 11
<211> LENGTH: 24
<212> TYPE: DNA
<213> ORGANISM: adeno-associated virus 2

<400> SEQUENCE: 11
cttccttcaa agaagcagta tcgg 24

<210> SEQ ID NO 12
<211> LENGTH: 24
<212> TYPE: DNA
<213> ORGANISM: Artificial Sequence
<220> FEATURE:
<223> OTHER INFORMATION: NEDDYLATION SITE DIRECTED MUTAGENESIS PRIMERS

<400> SEQUENCE: 12
ctggactctc ttccacaaaa cttc 24

<210> SEQ ID NO 13
<211> LENGTH: 22

-continued

```
<212> TYPE: DNA
<213> ORGANISM: adeno-associated virus 2

<400> SEQUENCE: 13

ggtcgctgga accatgtaaa ga                                        22


<210> SEQ ID NO 14
<211> LENGTH: 24
<212> TYPE: DNA
<213> ORGANISM: adeno-associated virus 2

<400> SEQUENCE: 14

gccagctcca atgactagaa cttt                                      24


<210> SEQ ID NO 15
<211> LENGTH: 23
<212> TYPE: DNA
<213> ORGANISM: adeno-associated virus 2

<400> SEQUENCE: 15

tccagaagga cataaacgag ctg                                       23


<210> SEQ ID NO 16
<211> LENGTH: 22
<212> TYPE: DNA
<213> ORGANISM: adeno-associated virus 2

<400> SEQUENCE: 16

ggacagatga ccagcttgaa gt                                        22


<210> SEQ ID NO 17
<211> LENGTH: 22
<212> TYPE: DNA
<213> ORGANISM: adeno-associated virus 2

<400> SEQUENCE: 17

gaacctacag acaaggtgga gc                                        22


<210> SEQ ID NO 18
<211> LENGTH: 24
<212> TYPE: DNA
<213> ORGANISM: adeno-associated virus 2

<400> SEQUENCE: 18

gctgctgtct tctcatcatt catc                                      24
```

PROCESS FOR PRODUCING A PLURALITY OF NEDDYLATION SITE MODIFIED AAV2 VECTORS

The content of the electronically submitted Sequence Listing (Name: Updated-Sequence-Listing.txt; Size: 3265 bytes; and last modified: Nov. 5, 2021) is herein incorporated by reference in its entirety.

FIELD OF THE INVENTION

The present invention is related to the study of Neddylation and conjugation of NEDD8 (neural-precursor-cell-expressed developmentally down-regulated 8) to its target proteins, more particularly it relates to process for producing a plurality of Neddylation site modified AAV vectors, Neddylation site modified AAV vectors and sequence for gene transfer used therein.

BACKGROUND

Gene therapy using Adeno-associated virus (AAV) has evolved significantly over the years by optimization of the vectors used in gene delivery. One of the major challenges during gene transfer with of AAV is the significant loss of vectors by intra-cellular defense mechanisms. Proteasome based degradation of the viral vectors has been a major rate-limiting step during the cytoplasmic trafficking of AAV in the host. While the role of ubiquitination of AAV capsid proteins during this process is well studied, the effect of Ubiquitin-like modifiers (UBLs) like Neddylation, which is known to facilitate cellular ubiquitination independently has not been known so far. The Neddylation involves covalent attachment of the NEDD8 protein to its substrates, which facilitates the targeted destruction of Neddylated proteins by proteasomes.

Recently, gene therapy has emerged as a potent tool in the field of molecular medicine. Various viral and non-viral systems have been explored for this purpose [Naldini L. Gene therapy returns to centre stage. Nature 2015]. Among the gene delivery tools available, recombinant Adeno-associated viruses (AAV) are attractive due to their relatively non-pathogenic nature, ability to transduce dividing and non-dividing cells as well as their long-term expression in infected cells [McCown T. Adeno-Associated Virus (AAV) Vectors in the CNS, 2005]. AAV is a non-enveloped virus having a single stranded genome of ~4.7 kb in size. AAV belongs to the Parvoviridae family and genus *Dependovirus* [Fields B N et al. Fields virology, 2007]. The capsid of AAV has an icosahedral symmetry which consists of proteins named VP1, VP2, VP3 in a ratio of 1:1:10 generated from alternative splicing of AAV genome and assembly activating protein (AAP) [Kerr, J. R. et al. Parvoviruses. J Chem Inf Model 2013; Johnson F B et al. Structural proteins of adenovirus-associated virus type 3. J Virol 1971; Rose J A et al. Structural Proteins of Adenovirus-Associated Viruses. J Viral 1971;]. AAV infects the host cell by binding to cell surface receptors and undergoes clathrin-mediated endocytosis followed by its intracellular trafficking and nuclear entry [Bartlett J S et al. Infectious entry pathway of adeno-associated virus and adeno-associated virus vectors, J Viral 2000]. Multiple AAV serotypes (AAV1-10) utilizes various cell surface receptors for their entry into host cells [Srivastava A. In vivo tissue-tropism of adeno-associated viral vectors, 2016]. Upon its entry, the virus is known to traffic towards the nucleus through different endosome compartments [Ding W. et al., Intracellular trafficking of adeno-associated viral vectors. Gene Ther 2005]. AAV escapes the endosome compartment into the cytosol due to the phospholipase (PLA2) activity present in the VP1 domain of capsid protein. Deletion and mutational studies for the PLA2 domain have demonstrated the inhibition of AAV to escape endosomes and compromise its transduction [Girod A et al. The VP1 capsid protein of adeno-associated virus type 2 is carrying a phospholipase A2 domain required for virus infectivity, 2002; Stahnke S et al., Intrinsic phospholipase A2 activity of adeno-associated virus is involved in endosomal escape of incoming particles, Virology Elsevier Inc. 2011; Grieger J C, Johnson J S, Gurda-Whitaker B. et al. Surface-Exposed Adeno-Associated Virus Vp1-NLS Capsid Fusion Protein Rescues Infectivity of Noninfectious Wild-Type Vp2/Vp3 and Vp3-Only Capsids but Not That of Fivefold Pore Mutant Virions. J Viral 2007]. Trafficking of AV through Golgi complex and endoplasmic reticulum have also been demonstrated through an indirect mechanism by using different small molecular inhibitors for various transduction steps [Nonnenmacher M E et al., Syntaxin 5-dependent retrograde transport to the trans-Golgi network is required for adeno-associated virus transduction. J Viral 2015]. After its escape from endosomes, AAV has to enter the nucleus in order to initiate the gene expression.

Four essential regions (BR1-4) having a potential nuclear localization signal (NLS) have been identified in the AAV2 serotype, which is also conserved in other serotypes as well [Grieger J C et al., Separate Basic Region Motifs within the Adeno-Associated Virus Capsid Proteins Are Essential for Infectivity and Assembly. J Viral 2006]. It as also been reported that AAV2 enters the nucleus through nuclear pore complex (NPC) with importin-1 as host protein carrying rAAV2 through NPC [Grieger J C et al., Separate Basic Region Motifs within the Adeno-Associated Virus Capsid Proteins Are Essential for Infectivity and Assembly, J Viral 2006; Nicolson S C et al. Recombinant Adeno-Associated Virus Utilizes Host Cell Nuclear Import Machinery To Enter the Nucleus, J Viral 2014; and Sonntag F et al. Adeno-Associated Virus Type 2 Capsids with Externalized VP1NP2 Trafficking Domains Are Generated prior to Passage through the Cytoplasm and Are Maintained until Uncoating Occurs in the Nucleus, J Virol 2006]. Post-nuclear entry, AAV traffics from the nucleolus to nucleoplasm, where it uncoats and initiate the gene expression [Qiu J et al., A 110-kDa nuclear shuttle protein, nucleolin, specifically binds to adeno-associated virus type 2 (AAV-2) capsid, Virology 1999; Bevington J M et al. Adeno-associated virus interactions with B23/Nucleophosmin. Virology 2007; and Johnson J S et al. Enhancement of Adeno-Associated Virus Infection by Mobilizing Capsids into and Out of the Nucleolus. J Viral 2009].

It is well recognized that approximately 30% of AAV vectors can successfully, enter the nucleus while the rest are either not able to enter the cell or degraded by intra cytoplasmic degradation mechanisms [Xiao P J et al., Quantitative 3D tracing of gene-delivery viral vectors in human cells and animal tissues, 2012]. Post-translational modifications like phosphorylation and ubiquitination are the primary mechanisms responsible for viral capsid degradation by initiating proteasome degradation pathways [Yan Z et al., Ubiquitination of both Adeno-Associated Virus Type 2 and 5 Capsid Proteins Affects the Transduction Efficiency of Recombinant Vectors, J Viral 2002]. Various mutant AAV vectors have been developed to avoid to the capsid degradation, which also led to their substantial increase in transduction efficiency [Zhong L, et al. Next generation of adeno-associated virus 2 vectors: point mutations in tyrosines lead to high-efficiency transduction at lower doses, 2008; and Gabriel N et al. Bioengineering of AAV2 capsid at specific serine, threonine, or lysine residues improves its transduction efficiency in vitro and in vivo, Hum Gene Ther Methods 2013]. However, the role of other Ubiquitin-like modifiers (UBLs) like Neddylation is unknown in the context of the AAV life cycle.

In the field of gene therapy, treatment of eye has gained importance over past two decades. Ocular gene therapy involves the introduction of an exogenous gene product to a host's cellular and genetic machinery for endogenous production of a desired gene product. The reason for this increase in interest is perhaps an increasing recognition that the eye, owing to its visibility and accessibility, is an attractive target for gene therapy. Clinical trials and research is ongoing in this field to come up with improved treatment processes and techniques. However, present state of the art ocular gene therapy lacks the application of Neddylation in the field of creation of targeted AAV vectors for the ocular gene therapy.

Wherefore, there is a need for a process for modifying Neddylation site of an AAV vector for creating Neddylation site modified AAV vector for improving efficiency for ocular gene therapy.

SUMMARY OF THE INVENTION

This summary is provided to introduce a selection of concepts, in a simple manner, which are further elaborated in detailed description of the invention. This summary is neither intended to identify the key or essential inventive concept of the subject matter, nor to determine the scope of the invention. The key essential concept of this invention lies in the exploration of AAV vectors that are Neddylated at select residues on the viral capsid leading to its targeted destruction by the cellular proteasomal machinery.

In an embodiment of the present invention, a process for producing a plurality of Neddylation site modified AAV vectors. The process includes following steps: (a) predicting a plurality of Neddylation sites on AAV VP1 capsid protein sequence based on relatively high confidence targets, wherein the AAV VP1 capsid protein sequence being set forth in Protein ID-YP_680426.1; and (b) producing the plurality of Neddylation site modified AAV vectors based on predicted plurality of neddylation sites on AAV VP1 capsid protein sequence. The production of the plurality of Neddylation site modified AAV vectors comprises selecting predicted plurality of neddylation sites, having score less than 0.3, on AAV VP1 capsid protein sequence for site-directed mutagenesis, wherein the neddylation sites are selected; and mutating the selected Neddylation sites from Lysine (K) to Glutamine (Q) residues to produce plurality of Neddylation site modified AAV vectors. The AAV is selected from a group consisting AAV serotypes 1, 2, 3, 4, 5, 6, 7, 8, 9, 10 and other AAV variants thereof.

In a further embodiment of the process for producing a plurality of Neddylation site modified AAV vectors, the process also includes steps of purifying the produced plurality of Neddylation site modified AAV vectors; and packaging the purified plurality of Neddylation site modified AAV vectors.

In another embodiment, the process for producing a plurality of Neddylation site modified AAV vectors further comprises evaluating the plurality of Neddylation site modified AAV vectors by intraocular gene transfer in order to demonstrate improved retinal transduction in murine models in vivo.

In yet another embodiment, a plurality of Neddylation site modified AAV vectors produced by the process of producing a plurality of Neddylation site modified AAV vectors is provided.

In an embodiment, a set of primers for analyzing gene expression of Neddylation pathway genes is provided. The set of primers include first primer for Neddylation target gene APPBP1, wherein gene sequences of the first primer being set forth in SEQ ID NO. 6; second primer for Neddylation target gene UBA3, wherein gene sequences of the first primer being set forth in SEQ ID NO. 7; third primer for Neddylation target gene UBC12, wherein gene sequences of the first primer being set forth in SEQ ID NO. 8; and fourth primer for Neddylation target gene NEDD8, wherein gene sequences of the first primer being set forth in SEQ ID NO. 9.

To further clarify the advantages and features of the present invention, a more particular description of the invention will follow with reference to specific embodiments thereof, which are illustrated in the appended figures. It is to be appreciated that these figures depict only typical embodiments of the invention and are therefore not to be considered limiting in scope. The invention will be described and explained with additional specificity and detail with the appended figures.

BRIEF DESCRIPTION OF THE ACCOMPANYING DRAWINGS

The disclosure will be described and explained with additional specificity and detail with the accompanying figures in which:

FIG. 1 is a graph plot of percentage GFP positive cells vs. treatment condition, where the graph depicts transduction efficiency of scAAV2 vectors in cells pre-treated with a small molecular inhibitor of Neddylation in the context of the invention;

FIGS. 2*a*, 2*b*, 2*c* and 2*d* are graph plots for relative normalised expression vs. time point for analysis for APPBP1, NEDD8, UBA3 and UBC 12, respectively, depicting quantitative PCR analysis of Neddylation pathway genes in response to AAV2 infection in the context of the invention;

Figure 5A:
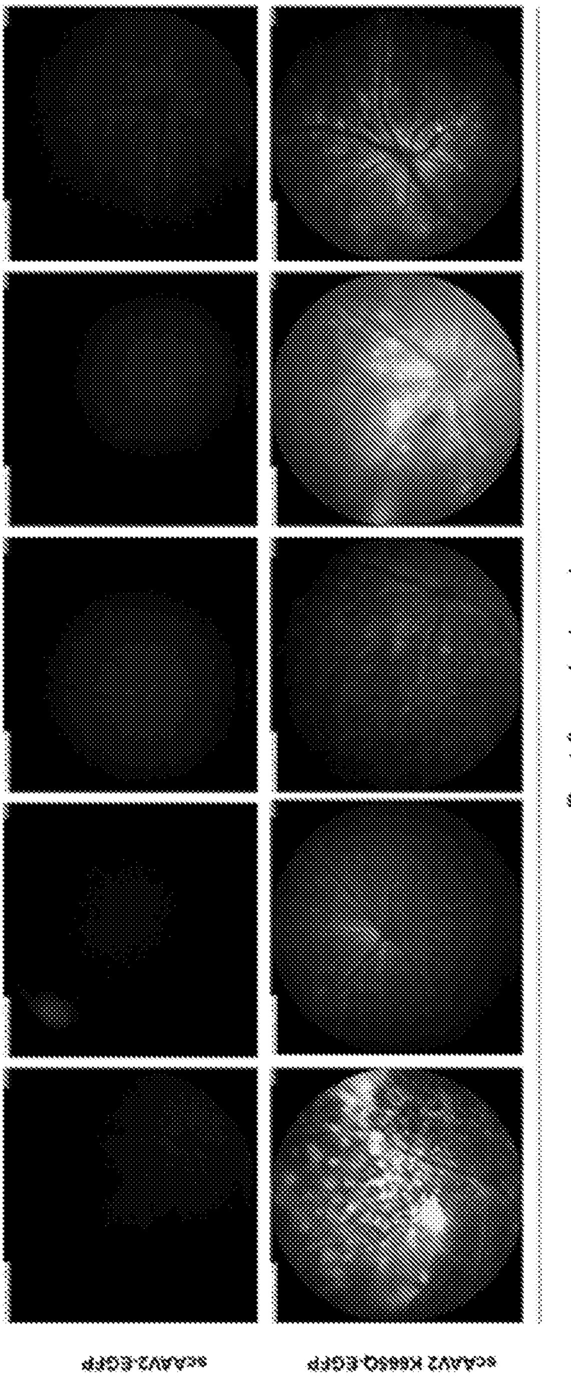
Figure 5B:
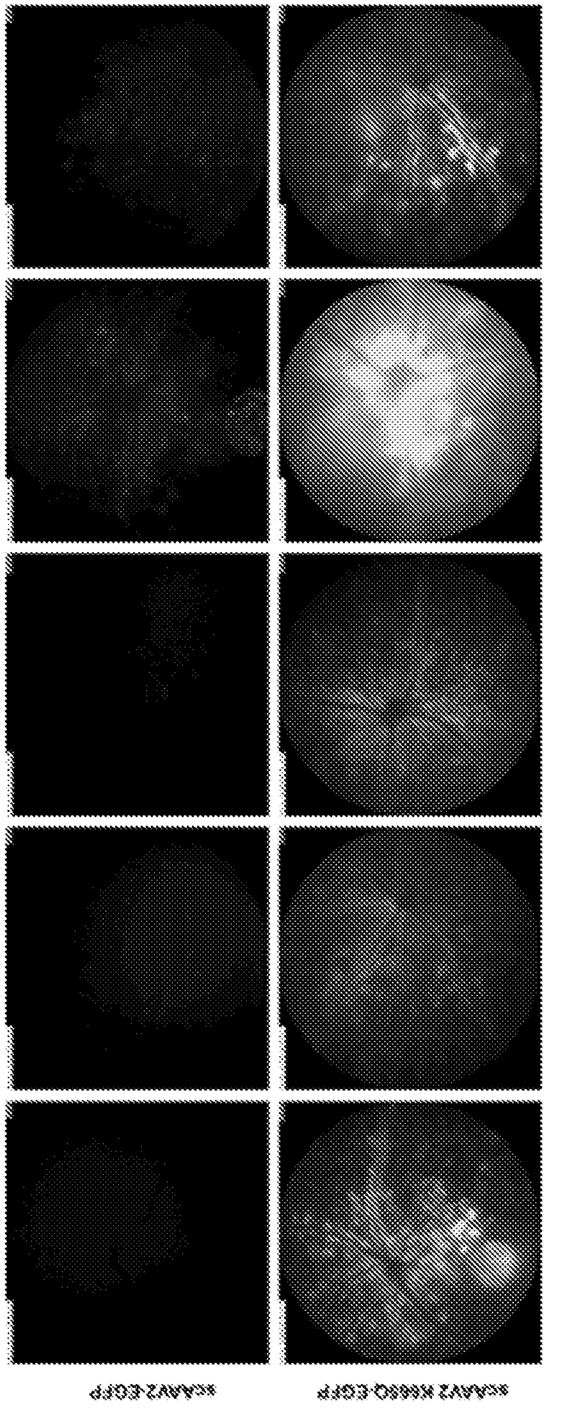
Figure 5C:
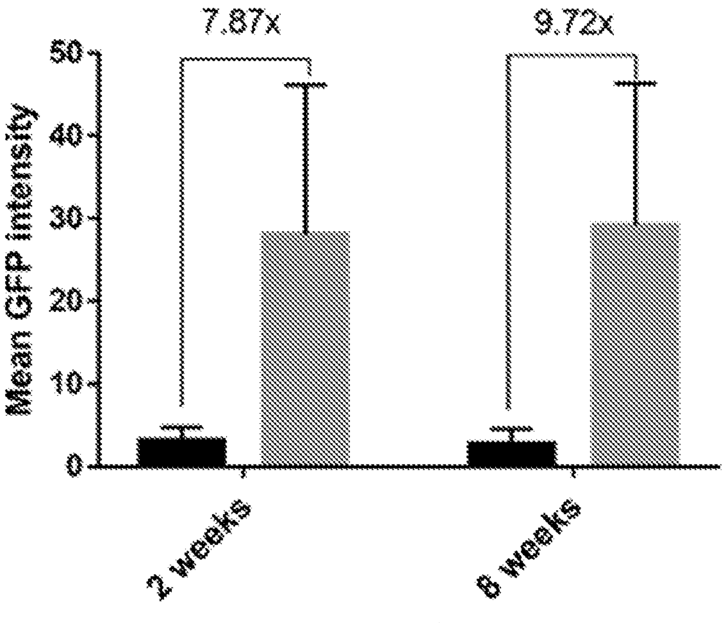

FIGS. 5A, 5B and 5C illustrate study of Ocular gene transfer in C57BL6/J mice with Neddylation mutant AAV2 vectors. Imaging was done at post 2 weeks (FIG. 5A) and 8 weeks (FIG. 5B) of injection, where eyes of C57BL6/J mice were mock injected or injected with scAAV2-EGFP and scAAV2 K665Q-EGFP by intravitreal route. FIG. 5C is a graph plot between the mean GFP intensity and time point of analysis.

FIG. 6 Neddylation site modified vectors expressing RPE65 demonstrate phenotypic rescue in rd12 mice model. Eyes of rd12 mice were mock-injected or injected with ssAAV2-RPE65 and ssAAV2K665Q-RPE65 vectors at a dose of $7\times10^{8}$ vectors via subretinal route. Scotopic electroretinogram (ERG) recordings were performed 6 weeks post vector administration. Completely opaque eyes caused by injury were eliminated from the recording data set. Dunnett's multiple comparisons test was used to determine the statistical significance. Data are mean±SD (n=5 to 7 eyes per experimental group). *P≤0.001 P≤0.01 *P≤0.05.

Figure 7:
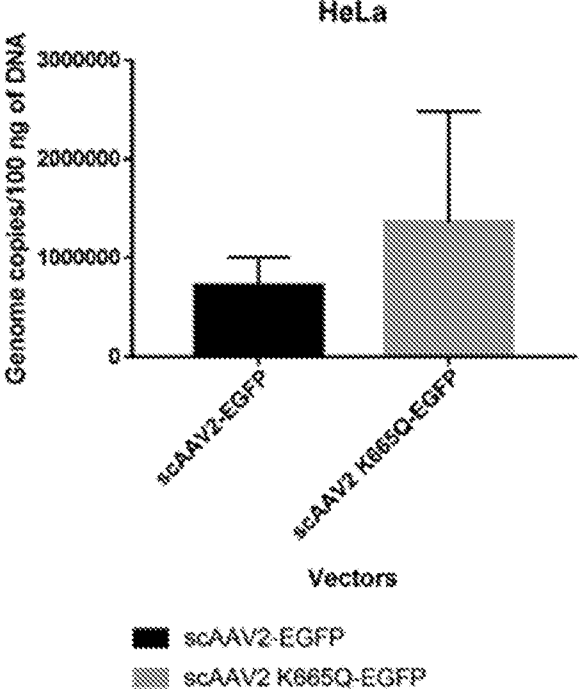
Figure 8:
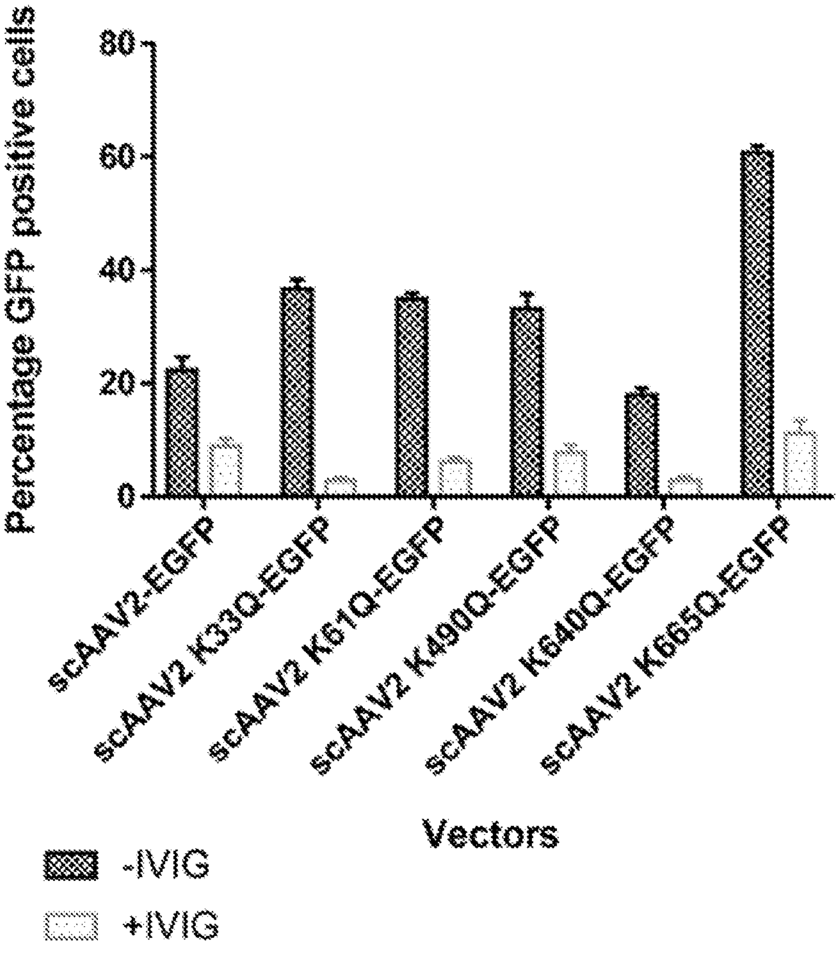

The FIG. 7 is a graph plot between genome copies per 100 ng of DNA and vectors depicting the entry profile of AAV2 wildtype and mutant vector in HeLa cells in vitro in the context of the invention; and The FIG. 8 is a graph plot between percentage GFP positive cells and vectors for an in vitro virus neutralization assay in the context of the invention.

Figure 9A:
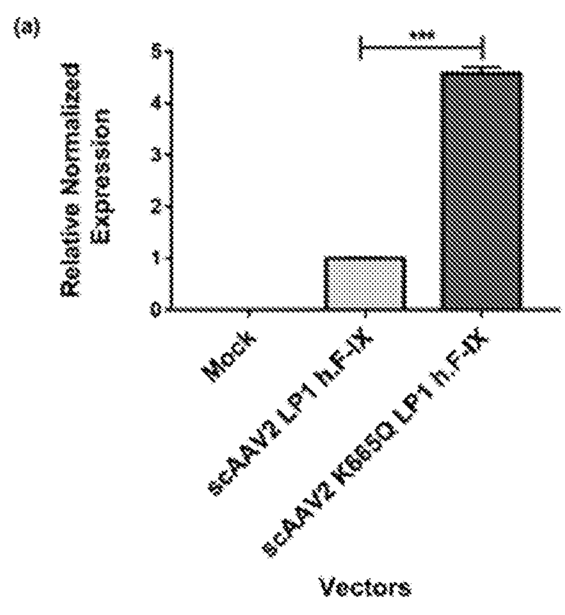

FIG. 9*a* illustrates Efficiency of Neddylation site modified AAV2 vectors for gene transfer into hepatic cells in vitro or in a murine model of hemophilia B, where Human factor IX (h.FIX) transcript levels assessed by quantitative PCR from Huh7 cells infected with scAAV2-h.FIX wildtype or mutant vectors are shown for depicting Efficiency of Neddylation site modified AAV2 vectors for gene transfer into hepatic cells in vitro or in a murine model of hemophilia B.

Figure 9B:
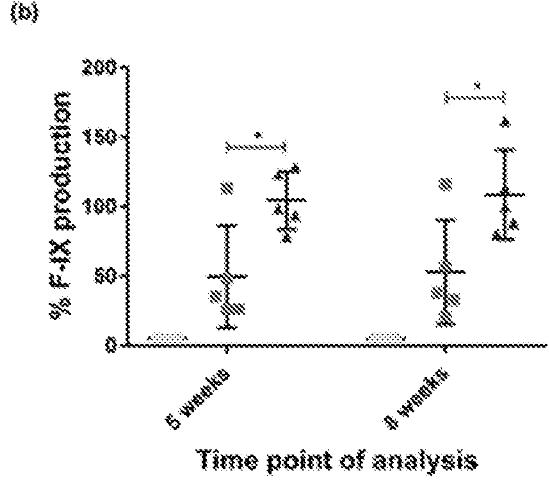

FIG. 9*b* illustrates Efficiency of Neddylation site modified AAV2 vectors for gene transfer into hepatic cells in vitro or in a murine model of hemophilia B, where levels of h.F-IX in plasma was determined 5 weeks and 8 weeks after injection of $5\times10^{10}$ vgs of AAV2 vectors per animal for depicting. Dunnett's multiple comparisons test was used to determine the statistical significance. Data are mean±SD (n=5 animals per experimental group). ***P≤0.001 *P≤0.05.

Figure 10:
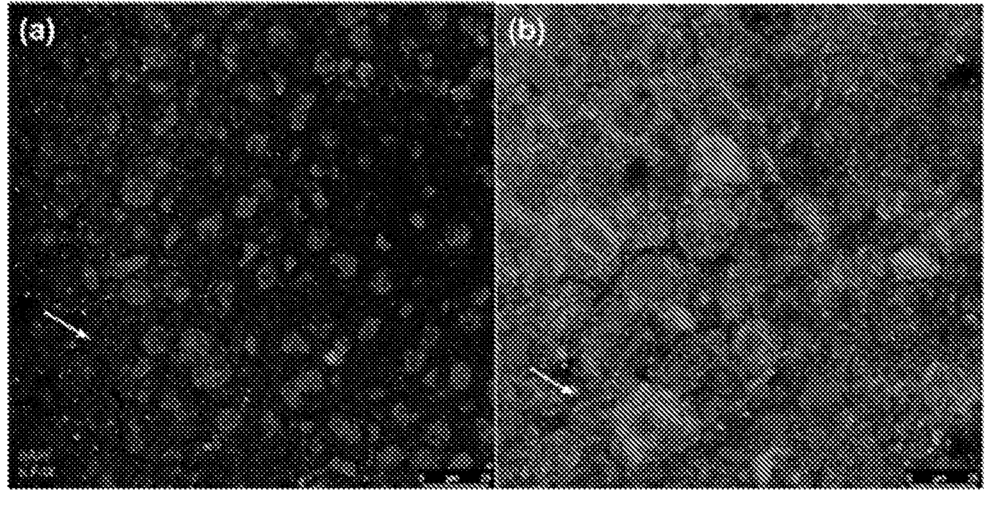

FIG. 10 illustrates immunohistochemistry for human factor TX after hepatic gene transfer in vivo, where Human factor IX (h.FIX) expression was detected by fluorescence microscopy 9 weeks post-injection of $5\times10^{10}$ vgs/animal of either scAAV2 LP1-h.FIX (a), scAAV2 K665Q LP1-h.FIX (b). Representative images are shown. Multiple bright non-specific fluorescent spots were detected (marked by arrow) surrounding specific signals during imaging. Original magnification ×400.

FIGS. 11*a-d* illustrates immune response in hemophilia B mice administered with AAV2 wild type or mutant vectors, where blood samples collected at nine weeks after hepatic gene transfer were assessed for T-cell and B-cell markers by flow cytometry. Data for Cytotoxic T cells (CD3+CD8+) (a); Helper T cells (CD3+CD4+) (b); regulatory T cells (CD4+ CD25+& FoxP3) in splenocytes (c); B-lymphocytes (d) from mock (PBS) injected or AAV2 administered animals are shown. Dunnett's multiple comparisons test was used to determine the statistical significance. Data are from mean±SD from 5 animals per group.

FIGS. 12*a-b* illustrates IFN-γ based ELISPOT assay to measure AAV2 capsid specific T-cell response, where FIG. 12*a* graph shows the number of spots generated by $1\times10^{6}$ splenocyte cells stimulated by AAV2 capsid specific peptide; and FIG. 12*b* depicts representative images of generated spots from each group is shown and Concavalin A was used as the positive control. Dunnett's multiple comparisons test was used to determine the statistical significance. Data are shown as mean±SD of the number of spots obtained from splenocytes seeded in duplicate wells for each of the five mice per group. p values were not significant (ns-p>0.05) Vs. mock injected hemophilia B mice.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE INVENTION

For the purpose of promoting an understanding of the principles of the invention, reference will now be made to the embodiments illustrated in the figures and specific language will be used to describe them. It will nevertheless be understood that no limitation of the scope of the invention is thereby intended. Such alterations and further modifications in the illustrated process, and such further applications of the principles of the invention as would normally occur to those skilled in the art are to be construed as being within the scope of the present invention.

It will be understood by those skilled in the art that the foregoing general description and the following detailed disclosure are exemplary and explanatory of the invention and are not intended to be restrictive thereof.

The terms "comprises", "comprising", or any other variations thereof, are intended to cover a non-exclusive inclusion, such that a process or method that comprises a list of steps does not include only those steps but may include other steps not explicitly listed or inherent to such a process or method. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this invention belongs. The system, methods, and examples provided herein are only illustrative and not intended to be limiting.

Embodiments of the present invention will be described below in detail with reference to the accompanying figures.

The present invention provides for a process for producing a plurality of Neddylation site modified AAV vectors.

The Neddylation is a post-translational modification that was reported in human cells in a CUL4A protein. This process has similarities with ubiquitin machinery. The process of Neddylation is a reversible mechanism where NEDD8 (neural precursor cell expressed developmentally down-regulated 8) protein binds to its substrate and alters the function of its targets. Neddylation is operated by a set of conserved enzymes named E1, E2, and E3 ligases. First, the NEDD8 is activated through an ATP dependent mechanism by an E1 enzyme (APPBP1/UBA3). Further. NEDD8 is transferred to an E2 conjugating enzyme (UBC12), and finally, E3 ligase transfers NEDD8 to its substrate. The NEDD8 and its substrate complexes are cleaved by the deneddylase enzymes, based on known techniques. The E1 and E2 enzymes of Neddylation pathway are conserved from yeast to mammals, but there are different E3 enzymes reported for different targets. The Neddylation majorly targets cullin-RING ligase (CRLs) as its substrates, which results in their activation. CRLs belongs to the family of E3 enzymes of Ubiquitin pathway, so the Neddylation, in turn, activates ubiquitination. Recently, Neddylation has also been reported to alter the P53 activity and cancer progression suggesting a plethora of its unknown targets. The present invention explores the role of Neddylation during AAV transduction and provides for process of modifying Neddylation site of a given AAV vector and creating Neddylation site modified AAV vector which may augment its gene transfer efficiency. The present invention has employed a series of in silico, biochemical and molecular biology approaches in order to study the role of Neddylation during AAV infection with an emphasis on its ability to transduce retinal cells in vitro and in vivo.

In an embodiment of the present invention, a process for producing a plurality of Neddylation site modified AAV vectors is provided. The process includes following steps: (a) predicting a plurality of Neddylation sites on AAV VP1 capsid protein sequence based on relatively high confidence targets, wherein the AAV VP1 capsid protein sequence being set forth in Protein ID-YP_680426.1; and (b) producing the plurality of Neddylation site modified AAV vectors based on predicted plurality of neddylation sites on AAV VP1 capsid protein sequence. The production of the plurality of Neddylation site modified AAV vectors comprises selecting predicted plurality of neddylation sites, having score less than 0.3, on AAV VP1 capsid protein sequence for site-directed mutagenesis, wherein the neddylation sites are selected; and mutating the selected Neddylation sites from Lysine (K) to Glutamine (Q) residues to produce plurality of Neddylation site modified AAV vectors.

In an embodiment, the AAV is selected from a group consisting AAV serotypes 1, 3, 4, 5, 6, 7, 8, 9, 10 and other AAV variants thereof.

In a specific embodiment of the present invention, the AAV used herein is a AAV2 serotype.

The process comprises Neddylation of AAV vectors at select residues on its viral capsid, leading to its targeted destruction by the cellular proteasomal machinery. In such embodiment, first small molecule inhibitors of NEDD8 protein is used in AAV infected cells and observed that global modulation of Neddylation enhanced AAV2 transduction (up to 50%) in vitro. It is also observed that Neddylation specific genes were significantly modulated in response to AAV2 infection during a targeted transcriptome screen of Neddylation pathway in HeLa cells. The process also includes characterising the capsid residues that could be Neddylated. In an embodiment, for performing the characterisation an in silico prediction strategy is employed by using an online tool NeddyPreddy® that identified nine lysine residues as potential targets. The process also includes, selecting top five targets out of the potential targets that may be abolished by site-directed mutagenesis. The process also includes evaluating the mutant vectors in at least three different cell lines. Based on the experiments, a K665Q mutant vector has a significantly improved transduction from HeLa (up to 150%) Huh7 (up to 46%), and ARPE19 (up to 165%) cells. The process also includes further evaluating the mutant vector by intraocular gene transfer in order to demonstrate improved retinal transduction in murine models in vivo. Hepatic gene transfer of the novel vectors developed [AAV2-K665Q-factor (F) IX] in hemophilia B mice demonstrated a significantly improved human coagulation FIX expression (up to 2-fold). The present invention for the first time highlights the role of Neddylation during AAV infection and its impact on generating novel AAV vectors with improved efficiency for ocular and hepatic gene therapy.

In a further embodiment of the process for producing a plurality of Neddylation site modified AAV vectors, the process also includes steps of purifying the produced plurality of Neddylation site modified AAV vectors; and packaging the purified plurality of Neddylation site modified AAV vectors.

In another embodiment, the process for producing a plurality of Neddylation site modified AAV vectors further comprises evaluating the plurality of Neddylation site modified AAV vectors by intraocular gene transfer in order to demonstrate improved retinal transduction in murine models in vivo.

In yet another embodiment, a plurality of Neddylation site modified AAV vectors are provided which are produced by the process of producing a plurality of Neddylation site modified AAV vectors.

In an embodiment, a set of primers for analyzing gene expression of Neddylation pathway genes is provided. The set of primers include first primer for Neddylation target gene APPBP1, wherein gene sequences of the first primer being set forth in SEQ ID NO. 6; second primer for Neddylation target gene UBA3, wherein gene sequences of the first primer being set forth in SEQ ID NO. 7; third primer for Neddylation target gene UBC12, wherein gene sequences of the first primer being set forth in SEQ ID NO. 8; and fourth primer for Neddylation target gene NEDD8, wherein gene sequences of the first primer being set forth in SEQ ID NO. 9.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods

For performing the experiments in the context of the present invention the following materials have been used: HuH-7 cell line was acquired from Dr. Saumitra Das, IISc, Bangalore. HeLa cell line was obtained from American Type Culture Collection (ATCC, Manassas, USA). ARPE19 cell line was obtained from Dr. Sowmya Parameswaran, Sankara Nethralaya, Chennai. The cells were cultured in Complete Iscove's Modified Dulbecco's Medium (IMDM) (Gibco, Life Technologies, Carlsbad. USA) with 10% Fetal Bovine Serum (Gibco, Life Technologies, Carlsbad, USA) at 37° C. with 5% CO2, supplemented with Ciprofloxacin (HiMedia Laboratories, Mumbai, India) and Piperacillin (MP Biomedicals, LLC, USA) at 10 μg/ml each. Small molecular inhibitor for NAE1, MLN4924 was obtained from Calbiochem (Merck, Kenilworth, USA). SYBR green qPCR mastermix was obtained from Promega (Madison. USA). C57BL6/J strain of mice was obtained from Jackson Laboratory (Bar Harbor, USA).

In Vitro Drug Assays

Approximately $3\times10^4$ HeLa cells were seeded in 24 well plate and incubated for 12 hours in Iscove's-modified Dulbecco's medium (IMDM) with 10% fetal bovine serum in humidified conditions and 5% CO2. Cells were either mock treated or treated with a Neddylation inhibitor, MLN4924 (Calbiochem, Merck, Kenilworth, USA) at a concentration of 1 μM and incubated at 37° C. for 3 hours. After incubation, cells were infected with scAAV2-EGFP vectors at a multiplicity of infection (MOI) of 5000 for 3 hours in IMDM at 37° C. Forty-eight hours later, the transgene (GFP) expression was quantified by flow cytometry (BDaccuri, BD Biosciences, Franklin Lakes, USA).

Targeted Transcriptome Analysis for Neddylation Pathway

Total RNA from each of the treated condition in HeLa cells was extracted by TRIzol reagent (Thermo Fisher, Waltham, USA). About 1 μg of RNA was used to convert cDNA by Verso cDNA synthesis kit (Thermo Fisher). The primers used for Neddylation gene targets were procured from Imperial Life Sciences (ILS, Gurgaon, India). Transcript levels of Neddylation target genes APPBP1, UBA3, UBC12, NEDD8 (Table 1) were measured by quantitative (q)PCR in a CFX97 Real-Time system (Biorad, Hercules, USA) with beta-actin as an endogenous control for the normalization of data.

TABLE 1

Primers designed for analyzing gene expression of Neddylation pathway genes.

| Pathway Enzyme | Name | Primer | Length (bp) | Tm (° C.) | Seq No. | Amplicon length (bp) |
|---|---|---|---|---|---|---|
| E1 | APPBP1 | 5'-CTTCCTTCAAAGAAGCAGTATCGG-3' | 24 | 57.5 | 11 | 139 |
| | | 5'-CTGGACTCTCTTCCACAAAACTTC-3' | 24 | 57.3 | 12 | |
| E1 | UBA3 | 5'-GGTCGCTGGAACCATGTAAAGA-3' | 22 | 58 | 13 | 129 |
| | | 5'-GCCAGCTCCAATGACTAGAACTTT-3' | 24 | 58.9 | 14 | |
| E2 | UBC12 (UBE2M) | 5'-TCCAGAAGGACATAAACGAGCTG-3' | 23 | 58.04 | 15 | 97 |
| | | 5'-GGACAGATGACCAGCTTGAAGT-3' | 22 | 57.7 | 16 | |
| | NEDD8 | 5'-GAACCTACAGACAAGGTGGAGC-3' | 22 | 58 | 17 | 119 |
| | | 5'-GCTGCTGTCTTCTCATCATTCATC-3' | 24 | 57.9 | 18 | |

In Silico Prediction for Neddylation Sites on AAV2 VP1 Capsid Protein

AAV2 VP1 capsid protein sequence (Protein ID-YP_680426.1) was used to predict Neddylation sites with the online tool NEDDYPREDDY. This tool has medium and high threshold levels based on output generated by the support vector machine (SVM). For the present analysis, set the threshold to a medium setting to capture relatively high confidence targets.

TABLE 2

Primers designed for abolishment of predicted Neddylation sites from lysine to glutamine. The bold face and underline font indicates the site of mutation.

| Mutant | Neddylation site directed mutagenesis primers | Seq No | bp | Tm (° C.) | GC % |
|---|---|---|---|---|---|
| K33Q | 5'-AAACCTGGCCCACCACCACCA**C**AGCCCGCAGAGCGGCATAAGGA-3' | 1 | 44 | 94 | 63 |
| | 5'-TCCTTATGCCGCTCTGCGGGCT**G**TGGTGGTGGTGGGCCAGGTTT-3' | 2 | | | |
| K51Q | 5'-CTTCAACGGACTCGAC**C**AGGGAGAGCCGGTCAA-3' | 3 | 33 | 83 | 60 |
| | 5'-TTGACCGGCTCTCCCT**G**GTCGAGTCCGTTGAAG-3' | 4 | | | |
| K640Q | 5'-CATGGGTGGATTCGGACTT**C**AACACCCTCCTCCACAGAT-3' | 5 | 39 | 84 | 53 |
| | 5'-ATCTGTGGAGGAGGGTGTT**G**AAGTCCGAATCCACCCATG-3' | 6 | | | |
| K490Q | 5'-CCAGCAGCGAGTATCA**C**AGACATCTGCGGATAACAACAAC-3' | 7 | 40 | 82 | 50 |
| | 5'-GTTGTTGTTATCCGCAGTGTCT**G**TGATACTCGCTGCTGG-3' | 8 | | | |
| K665Q | 5'-ACCACCTTCAGTGCGGCA**C**AGTTTGCTTCCTTC-3' | 9 | 33 | 80 | 54 |
| | 5'-GAAGGAAGCAAACT**G**TGCCGCACTGAAGGTGGT-3' | 10 | | | |

Vector Production

The top 5 sites predicted for Neddylation based on score>0.3 were chosen for further sitedirected mutagenesis (Table 2). Neddylation targets were mutated from Lysine (K) to Glutamine (Q) residues by using Quick-change II XL site-directed mutagenesis kit (Agilent Technologies, city, country) as per the manufacturer's instructions. Viral vectors were packaged and purified as described earlier. Briefly, forty 150-mm2 dishes, 80% confluent with AAV-293 cells were transfected with AAV2 (rep/cap) or AAV2 mutant (rep/cap) vectors, transgene (p.dsAAV2-EGFP) vectors, and AAV-helper (p.helper) vectors. Cells were collected 68-72 hours post-transfection, lysed and treated with benzonase nuclease (25 units/ml; Sigma-Aldrich. St. Louis, USA). Further, the vectors were purified by iodixanol gradient ultracentrifugation (OptiPrep; Sigma-Aldrich) followed by column chromatography (HiTrap SP column; GE Healthcare Life Sciences, Chicago, USA). The vectors were concentrated to a final volume of 0.5 ml in phosphate-buffered saline (PBS), using Amicon Ultra 10K centrifugal filters (Millipore Burlington, USA). Physical titers were quantified by qPCR as per the process disclosed by Aumhammer C, Haase M, Muether N, et al., Universal Real-Time PCR for the Detection and Quantification of Adeno-Associated Virus Serotype 2-Derived Inverted Terminal Repeat Sequences. Hum Gene Tuer Methods 2012.

Transduction Assays In Vitro

About, $3\times10^4$ cells per well were seeded in 24 well plate and incubated for 12 hours in IMDM with 10% fetal bovine serum in humidified conditions and 5% $CO_2$. Cells were mock infected or infected with scAAV2-EGFP and scAAV2-EGFP mutant vectors for 3 hours. Forty-eight hours later, the transgene (GFP) expression was quantified by flow cytometry (BD accuri).

Virus Entry Assay

HeLa cells were seeded in 4 replicates at a density of $1\times10^5$ cells per well in a 24 well plate. Cells were mock infected or infected with scAAV2-EGFP and mutant viruses at a MOI of 10000. Cells were collected 3 hours post infection by trypsinization followed by genomic DNA isolation. Viral genomes were quantified against appropriate plasmid standards and with the PolyA site as a target for amplification by qPCR.

In Vitro Neutralization Assay

Approximately $3\times10^4$ HeLa cells were seeded per well in triplicates and incubated for 12 hours in Iscove's-modified Dulbecco's medium with 10% fetal bovine serum in humidified conditions and 5% CO2. For this assay, the AAV2 vectors were used at a MOI of 5000. The scAAV2-EGFP and the mutant vectors were incubated with 1:256 dilution of human intravenous immunoglobulin (IVIG) (10 mg/ml) (Baxter, Deerfield. USA) for 1 hours at 37° C. Subsequently, cells were infected with mutant vectors and scAAV2-EGFP alone or with vectors that were preincubated with IVIG. Forty-eight hours later, the transgene (GFP) expression was quantified by flow cytometry (BD accuri).

Ocular Gene Transfer and Fluorescence Imaging

The present invention involved use of C57BL6/J mice. Studies were conducted on mice housed at 22-24° C. in individually ventilated cages in the context of the present invention. Mice had free access to water and food. All efforts were made to minimize any suffering during the present invention. Eyes of C57BL6/J mice were dilated by 1% Atropine (Jawa Pharmaceuticals India Pvt. Ltd. Gurgaon, India). Phenylephrine+Tropicamide (Sunways India Pvt. Ltd. Mumbai, India). Mice were anesthetized by intraperitoneal injection of ketamine (80 mg/kg) and Xylazine (12 mg/kg). For intravitreal administration, an opening was created at scelera near limbus by an insulin syringe, and 1 μl of AAV vector was injected through the same opening by Hamilton syringe fitted with 33 gauge beveled needle. After injections were completed, tobramycin (Sunways India Pvt. Ltd.) was applied to the eyes. Fluorescence imaging was performed after 2 and 8 weeks of vector administration, in Micron IV imaging system as per manufacturer's instructions (Phoenix Research Lab, Pleasanton, USA). Briefly, eyes of C57BL6/J mice were dilated by 1% Atropine (Jawa Pharmaceuticals India Pvt. Ltd), Phenylephrine+Tropicamide (Sunways India Pvt. Ltd.). Mice were anesthetized by intraperitoneal injection of ketamine (80 mg/kg) and xylazine (12 mg/kg). Further, 2.5% hypromellose (OCuSOFT, Rosenberg. USA) was applied to the eye before imaging. Intensity was set at maximum and gain was set at 15 db, the frame rate was set at 6 fps for imaging of all the groups. The fluorescence in the eyes of treated animals were further quantified by Image J analysis as described by Schneider C A. et al, NIH Image to ImageJ: 25 years of image analysis. Nat Methods Nature Publishing Group 2012; and Wassmer S J, et al. Exosome-associated AAV2 vector mediates robust gene delivery into the murine retina upon intravitreal injection. Sci Rep Nature Publishing Group 2017.

Electroretinography

For scotopic ERG measurement, mice were dark-adapted overnight. ERG was recorded as per the manufacturer's instruction (Phoenix research lab, Pleasanton, CA, USA). Briefly, mice were anesthetized with an intraperitoneal injection of ketamine (80 mg/kg) and Xylazine (12 mg/kg) followed by pupil dilation by Phenylephrine+Tropicamide (Sunways India Pvt. Ltd. Mumbai, India). Mice were placed on a heating pad and the reference electrode was subcutaneously placed under the forehead between the ears, while the ground electrode was placed under the tail subcutaneously. Corneal electrode was placed on the cornea after applying 2.5% Hypromellose (OCuSOFT, Rosenberg, NC, USA). ERG was recorded with the intensity of light flash varying between −1.7 to 3.1 log cd sec/$m^2$.

Hepatic Gene Transfer in Hemophilia B Mice

About $5\times10^{10}$ vector genomes of scAAV2 vectors or scAAV2 K665Q vectors containing LP1 promoter driven human FIX (scAAV2 LP1-h.FIX) were administered into 6 to 8 weeks old hemophilia B mice (n=5 animals per group), via the tail vein. PBS was administered into the control group of hemophilia B mice. Five and eight weeks after gene transfer, retro-orbital blood collection from all animals was performed and plasma isolated by standard methods. To assay the h.FIX activity in murine plasma, performed an enzyme-linked immunosorbent assay (ELISA) using a commercial kit (Asserachrom IX: Ag, Diagnostica Stago, Asnières, France).

Immunohistochemistry

For immunostaining of human FIX, murine liver samples were harvested after 9 weeks of hepatic gene transfer. Samples were embedded in OCT media (Polyfreeze, Sigma Aldrich), sectioned at 10 μm thickness and fixed in 4% paraformaldehyde for 15 mins at room temperature. Slides were washed with PBS and blocked in a solution containing 10% normal donkey serum (Santa Cruz Biotechnology, Dallas. TX, USA), 0.2% Triton X-100 (Sigma Aldrich) diluted in PBS for 1 hr. at room temperature. Subsequently, sections were incubated with goat anti-human FIX antibody (1:100, Affinity Biologicals. Hamilton, ON, Canada) overnight at 4° C. After washing thrice, the slides were incubated with donkey anti-goat Cy3 antibody (Jackson ImmunoReasearch, West Grove, PA, USA,) at dilution of 1:500 for 1.5 hrs. at room temperature. Sections were washed thrice and mounted with Fluoroshield™ with DAPI (Sigma Aldrich). Images were acquired by Leica DMi8 confocal microscope (Wetzlar, Germany).

Immune Assays

To examine the immunogenicity associated with hepatic gene transfer of AAV2 vectors, we enumerated the T-cell, B-cell and T-reg cells in hemophilia B mice that received h.FIX gene therapy. Briefly, peripheral blood from hemophilia B mice was collected 9 weeks after gene transfer. After RBC lysis (155 mM $NH_4Cl$, 12 mM $NaHCO_3$ & 0.1 mM EDTA), samples were incubated with a combination of FITC labeled anti-CD3, PE-labelled anti-CD8, PerCP labeled anti-CD4 and APC labeled anti-CD19 (BD Biosciences) antibodies for 30 mins at room temperature and percentage CD3+. CD4+, CD8+, and CD19+ cells were assessed by flow cytometry (BD Accuri C6 Plus). To profile the T-reg cells in murine splenocytes, ~2 million cells were stained with PerCP labeled anti-CD4 and APC labeled anti-CD25 and PE-conjugated Foxp3 antibodies as per the manufacturer's protocol (BD Biosciences).

ELISPOT Assay

Splenocytes from control or treated mice were harvested and samples processed as described by Hareendran S. Ramakrishna B, and Jayandharan G R (Synergistic inhibition of PARP-1 and NF-κB signaling downregulates immune response against recombinant AAV2 vectors during hepatic gene therapy. Eur J Immunol 2016; 46:154-66.) Briefly, after RBC lysis, ~$1\times10^6$ viable splenocytes were stimulated with 2 μg/mL of AAV2 capsid T-cell epitope specific peptide (SNYNKSVNV) (JPT Peptide Technologies. GmbH, Germany) and seeded into IFN-γ antibody pre-coated ELISPOT plate (MabTech, Ohio, USA). Concanavalin A (2 μg/mL) was used as positive control for the assay. After 36 hrs of incubation at 37° C., spots were developed using BCIP/NBT. Spot forming units (SFU) and the images were captured in an ELISPOT reader (AID reader, GmbH, Germany).

Statistical Analysis

Statistical analysis was performed by either Student's t-test or ANOVA by GraphPad Prism 7 (GraphPad, La Jolla, USA). Values obtained between the test and control groups were considered to be statistically significant if the p value was <0.05. p values at various confidence intervals are denoted as *p<0.05, p<0.01, *p<0.001.

Results

Figure 1:
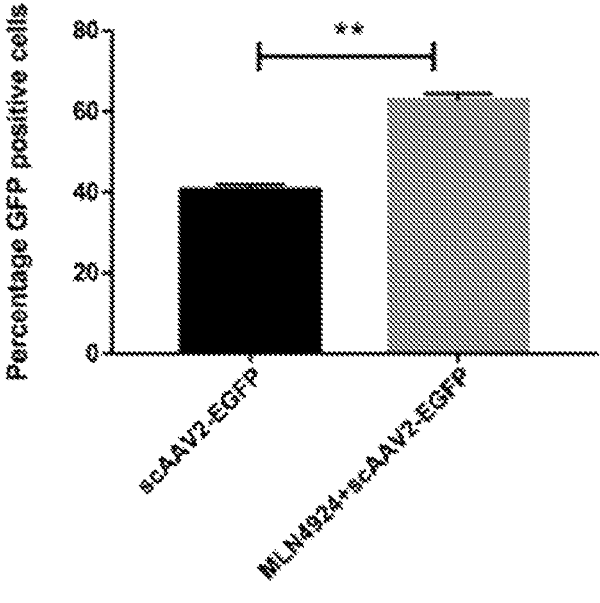
Figure 2:
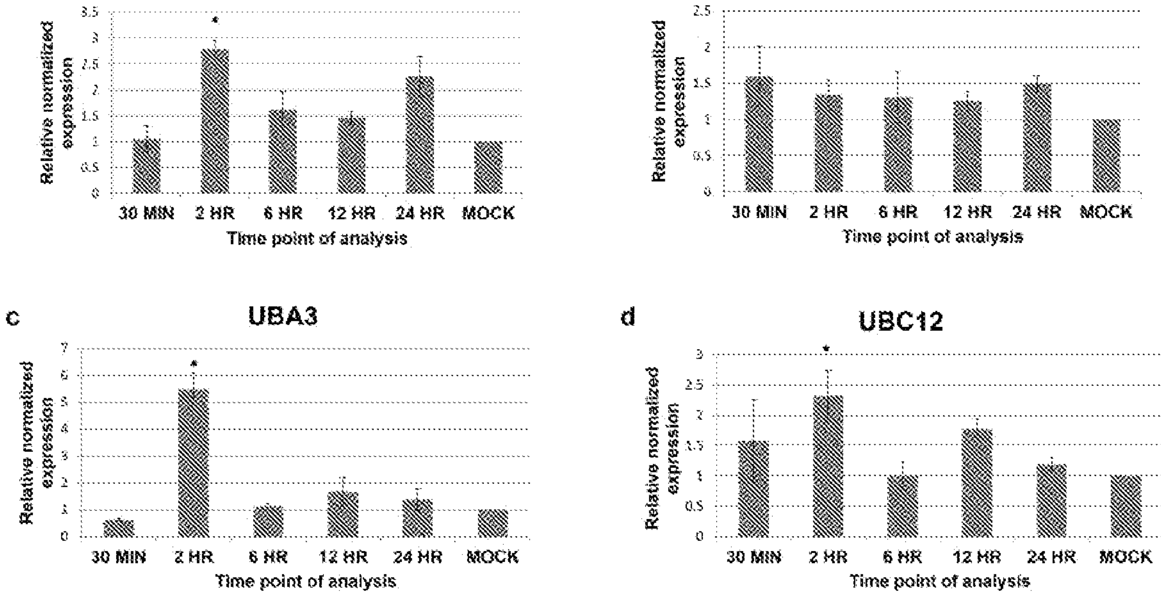

Inhibition of Host Cellular Neddylation Improves Transduction of AAV2 Vectors In Vitro To determine the role of cellular Neddylation during AAV2 infection, a small molecular inhibitor of Neddylation being used herein, MLN4924. The MLN4924 prevents the formation of the NEDD8 and Neddylation activating enzyme (NAE1) protein complex. The HeLa cells were pre-treated for three hours, after which the HeLa cells were infected with scAAV2-EGFP. Analysis of transgene expression demonstrates a significant increase (62.92% vs. 40.71% in control cells) in transduction when the cells are pre-treated with Neddylation inhibitors. This suggests that cellular Neddylation could be a rate-limiting step during AAV2 transduction. Further studies such as specific targeting of Neddylation pathway genes by RNA interference are warranted to understand the mechanism involved in this process. FIG. 1 is a graph plot of percentage GFP positive cells vs. treatment condition, where the graph depicts transduction efficiency of scAAV2 vectors in cells pre-treated with a small molecular inhibitor of Neddylation in the context of the invention. Approximately $3\times10^4$ HeLa cells were seeded in 24 well plate and incubated for 12 hours in Iscove's-modified Dulbecco's medium (IMDM) with 10% fetal bovine serum in humidified conditions and 5% CO2. The HeLa cells were either mock treated or treated with a Neddylation inhibitor. MLN4924 at a concentration of 1 μM and incubated at 37° C. for 3 hours. After incubation, cells were infected with scAAV2-EGFP vectors at a multiplicity of infection (MOI) of 5000 for 3 hours in IMDM at 37° C. Forty-eight hours later, the transgene (GFP) expression was quantified by flow cytometry. Data presented in FIG. 1 is a mean of 3 replicates. Error bars represent SD, n=3, **P≤0.01.

Specific Genes in Neddylation Pathway are Dysregulated Upon AAV2 Infection in HeLa Cells To determine the changes to Neddylation machinery during AAV2 infection, transcript levels of Neddylation pathway genes were examined by measuring the expression pattern of marker genes, including activating the enzyme (E1), a conjugating enzyme (E2) and the NEDD8 gene that are known to be important in regulating this pathway. Since multiple ligating enzymes (E3) are known for Neddylation in a substrate-specific manner, the mRNA level for E3 enzyme was not assessed. A time course analysis of the target genes in HeLa cells at 30 minutes, 2 hours, 6 hours, 12 hours, and 24 hours was performed after AAV2 infection. Upon normalizing the transcript levels with beta-actin transcript levels, it was observed that most of the Neddylation genes are upregulated as early as the 2-hours time point after infection. Several existing studies have indicated that AAV2 undergoes cytoplasmic trafficking during this time point in HeLa cells and thus it is conceivable that the changes in transcript levels of Neddylation genes indicate that this signalling pathway is activated upon AAV2 infection. FIGS. 2*a*, 2*b*, 2*c* and 2*d* are graph plots for relative normalised expression vs. time point for analysis for APPBP1, NEDD8, UBA3 and UBC 12, respectively, wherein the graphs depict quantitative PCR analysis of Neddylation pathway genes in response to AAV2 infection in the context of the invention. Approximately $8\times10^4$ HeLa cells were seeded in 12 well plate and incubated for 12 hours in Iscove's-modified Dulbecco's medium (IMDM) with 10% fetal bovine serum in humidified conditions and 5% CO2. The HeLa cells were either mock treated or treated with scAAV2-EGFP at MOI of 5000. Total RNA from each of the treated condition in the HeLa cells, was extracted by TRIzol. About 1 μg of RNA was used to convert cDNA. Transcript levels of Neddylation target genes APPBP1, UBA3, UBC12, NEDD8 (Table 2) were measured by quantitative (q)PCR in a CFX97 Real Time with beta-actin as an endogenous control for the normalization of data. Each time point of analysis had its own mock control. Data presented in figure is a mean of 3 replicates. Error bars represent SD, n=3 *P≤0.05

AAV2 Mutant Vectors Altered at Neddylation Sites Demonstrate an Increase in Transduction Efficiency The present involves shortlisting of the top five residues (cut off>0.3) predicted by the NeddyPreddy® program (Table 3) for further mutagenesis.

TABLE 3

Neddylation sites predicted by Neddypreddy ® on AAV2 VP1 capsid protein. *The numbering of amino acids in VP1 capsid protein is according to NCBI Protein ID-YP_680426.1.

| S.no. | Position* | Peptide | Score | Probability |
|---|---|---|---|---|
| 1 | 33 | 23-WKLKPGPPPP**K**PAERHKDDSR-43 | 1.09 | 0.53 |
| 2 | 640 | 630-PSPLMGGFGL**K**HPPPQILIKN-650 | 0.85 | 0.40 |
| 3 | 61 | 50-KYLGPFNGLD**K**GEPVNEADAA-70 | 0.66 | 0.30 |
| 4 | 490 | 480-GPCYRQQRVS**K**TSADNNNSEY-500 | 0.43 | 0.21 |
| 5 | 665 | 655-ANPSTTFSAA**K**FASHFITQYST-675 | 0.36 | 0.18 |
| 6 | 39 | 29-PPPPKPAERH**K**DDSRGLVLPG-49 | 0.18 | 0.13 |
| 7 | 24 | 14-TLSEGIRQWW**K**L**K**PGPPPPKP-34 | 0.16 | 0.13 |
| 8 | 161 | 151-VEPDSSSGTG**K**AGQQPARKRL-171 | 0.03 | 0.10 |
| 9 | 620 | 610-DVYLQGPIWA**K**IPHTDGHFHP-630 | 0.03 | 0.10 |

These included lysine residues at K33, K61. K490, K640, K665 in the VP1 protein, that were mutated to corresponding glutamine residues. The average viral titers for these mutants were not significantly different from wild type-vectors (Table 4).

TABLE 4

Physical particle titers for the vectors (scAAV2-EGFP and Neddylation mutants) generated in this study. The data is presented in vector genomes per mil (vgs/ml).

| Vector | Titer(vgs/ml) |
|---|---|
| scAAV2-EGFP | 2.00E + 3011 |
| scAAV2 K33Q-EGFP | 8.52E + 11 |
| scAAV2 K61Q-EGFP | 1.3E + 11 |
| scAAV2 K490Q-EGFP | 11.64E + 3012 |
| scAAV2 K640Q-EGFP | 1.56E + 3012 |
| scAAV2 K665Q-EGFP | 6.25E + 11 |

Figure 3:
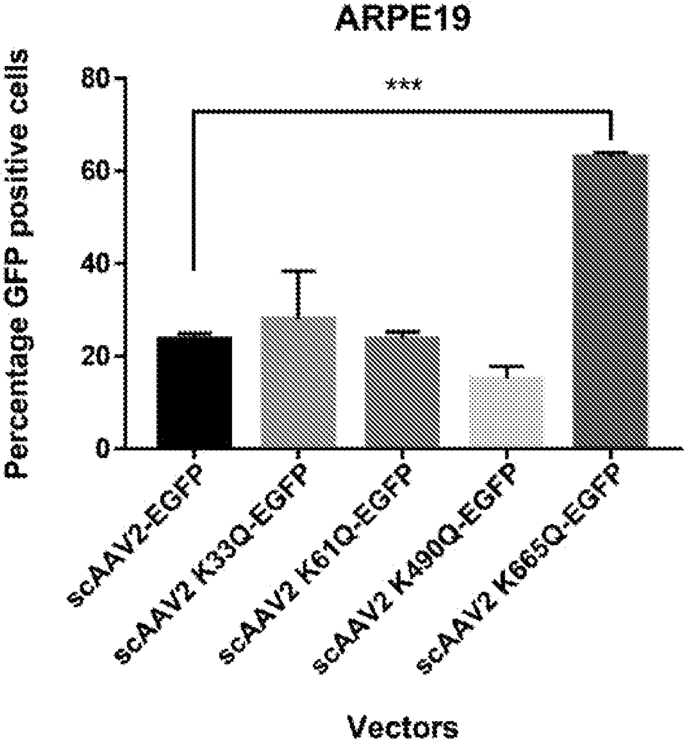
FIG. 3 is a graph plot between percentage GFP positive cells and vectors, depicting transduction efficiency of AAV2 mutant vectors in ARPE cells in vitro in the context of the invention.

These vectors (listed in Table 4) were further tested at a MOI of 5000 in retinal (ARPE) cells. The data from FACS analysis showed a significantly higher (63.15% vs. 23.81%) increase in EGFP gene expression in scAAV2 K665Q mutant vector treated cells in comparison to WT-AAV2 vectors. FIG. 3 is a graph plot between percentage GFP positive cells and vectors, depicting transduction efficiency of AAV2 mutant vectors in ARPE cells in vitro in the context of the invention. About, $3\times10^4$ ARPE19 cells per well were seeded in 24-well plate and incubated for 12 hr. in IMDM with 10% fetal bovine serum. The ARPE19 cells were mock infected or infected with scAAV2-EGFP and scAAV2-EGFP mutant vectors for 3 hours. Forty-eight hours later, the GFP expression was quantified by Flow cytometry. Data presented in FIG. 3 is a mean of 3 replicates. Error bars represent SD, n=3. ***P≤0.001

Figure 4A:
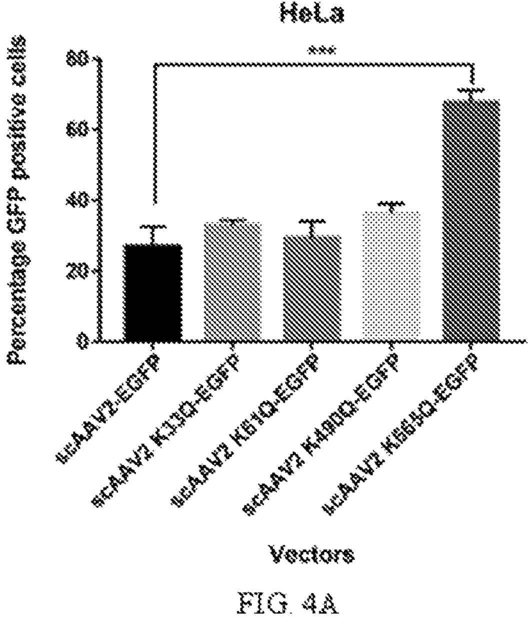
FIGS. 4A and 4B are graph plots between percentage GFP positive cells and vectors for HeLa cells and HuH7 cells, respectively, where the graph depicts transduction efficiency of AAV2 mutant vectors in the Huh7 and the HeLa cells in vitro in the context of the invention.
Figure 4B:
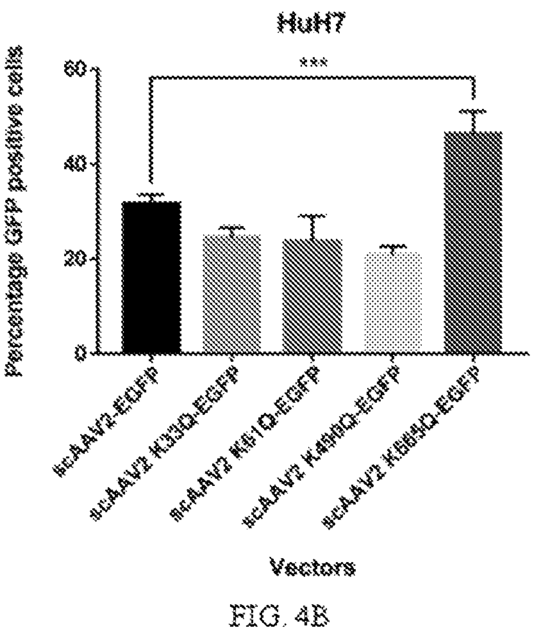

To further assess if the increase in transduction is cell-line specific, the present invention provides for use of two other cell lines, HeLa and Huh7. As can be seen in FIGS. 4A and 4B, the K665Q mutant demonstrated a similar increase in transgene expression in either HeLa (67.62% vs. 27.01%) or Huh7 cells (46.28% vs. 31.64%) suggesting that the mutant vector had superior infectivity in multiple cell types. The FIGS. 4A and 4B depict transduction efficiency of AAV2 mutant vectors in Huh7 and HeLa cells in vitro. About, $3\times10_4$ HeLa and HuH7 cells per well were seeded in 24-well plate and incubated for 12 hours in IMDM with 10% fetal bovine serum. The cells were mock infected or infected with scAAV2-EGFP and scAAV2-EGFP mutant vectors for 3 hours. Forty-eight hours later, the transgene (GFP) expression was quantified by flow cytometry. Data presented in figure is a mean of 3 replicates. Error bars represent SD, n=3. ***P≤0.001

The entry profile of scAAV2 K665Q was further assessed and it was found that entry of K665Q mutant was similar to WT-AAV2. It can be inferred from the FIG. 7 which is a graph plot between genome copies per 100 ng of DNA and vectors depicting the entry profile of AAV2 wildtype and mutant vector in HeLa cells in vitro in the context of the invention. The FIG. 7 illustrates entry profile of AAV2 wild-type and mutant vector in HeLa cells in vitro. The HeLa cells were seeded in 4 replicates at density of $1\times10^5$ cells per well in a 24 well plate. The cells were mock infected or infected with scAAV2-EGFP and mutant vectors at a MOI of 10000. Cells were collected 3 hours post-infection and genomic DNA was isolated as described in the known methods. Viral genomes were titered against the plasmid reference standard. Data presented in the FIG. 6 is a mean of 3 biological replicates with 3 technical replicates for each condition. Error bars represent SD, n=9.

Therefore, it was deduced that the increased transduction seen with K665Q mutant may be due to the circumvention of rate limiting step such as Neddylation during viral trafficking.

Mutant AAV2 Vector Demonstrates Superior Gene Transfer m the Mouse Retina

To determine the ocular gene transfer potential of the AAV2 mutant vector, the present invention provides for examining their efficacy by intravitreal administration into normal C57BL6/J mice. scAAV2-WT or the K665Q mutant vector containing EGFP as the transgene was administered at a dose of $3\times10^8$ vgs/eye (n=6 eyes per group). Consistent with aforementioned in vitro data, the K665Q mutant had 7.87 to 9.72 fold higher EGFP expression levels (FIGS. 5A, 5B and 5C), over a period of 2-8 weeks. One of the AAV2 K665Q vector injected eye, did not show any EGFP expression possibly due to variations in the manual injection procedure. These data demonstrate the therapeutic potential of AAV2 K665Q vector in general and for ocular gene transfer in particular.

The FIGS. 5A, 5B and 5C illustrate study of Ocular gene transfer in C57BL6/J mice with Neddylation mutant AAV2 vectors. Imaging was done at post 2 weeks (FIG. 5A) and 8 weeks (FIG. 5B) of injection. Eyes of C57BL6/J mice were mock injected or injected with scAAV2-EGFP and scAAV2 K665Q-EGFP by intravitreal route. For imaging, eyes were dilated by 1% Atropine, Phenylephrine+Tropicamide. Mice were anesthetized by intraperitoneal injection of ketamine (80 mg/kg) and Xylazine (12 mg/kg), 2.5% Hypromellose was applied to the eye before imaging. Intensity was set at maximum and gain was set at 15 db. Frame rate was set at 6 fps for imaging of all the groups. Imaging was done at post 2 weeks and 8 weeks of injection. Image analysis was done by using Concentric Circle Plugin in ImageJ software. n=5 eyes. FIG. 5C is a graph plot between the mean GFP intensity and time point of analysis.

Figure 6A:
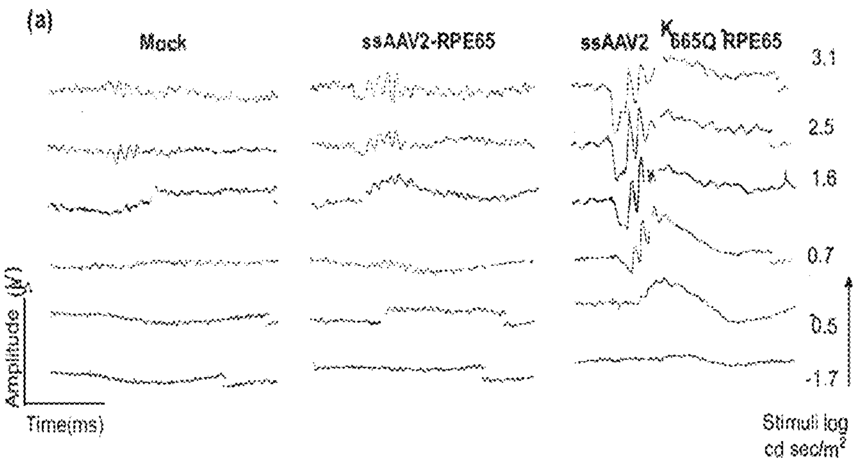
Figure 6B:
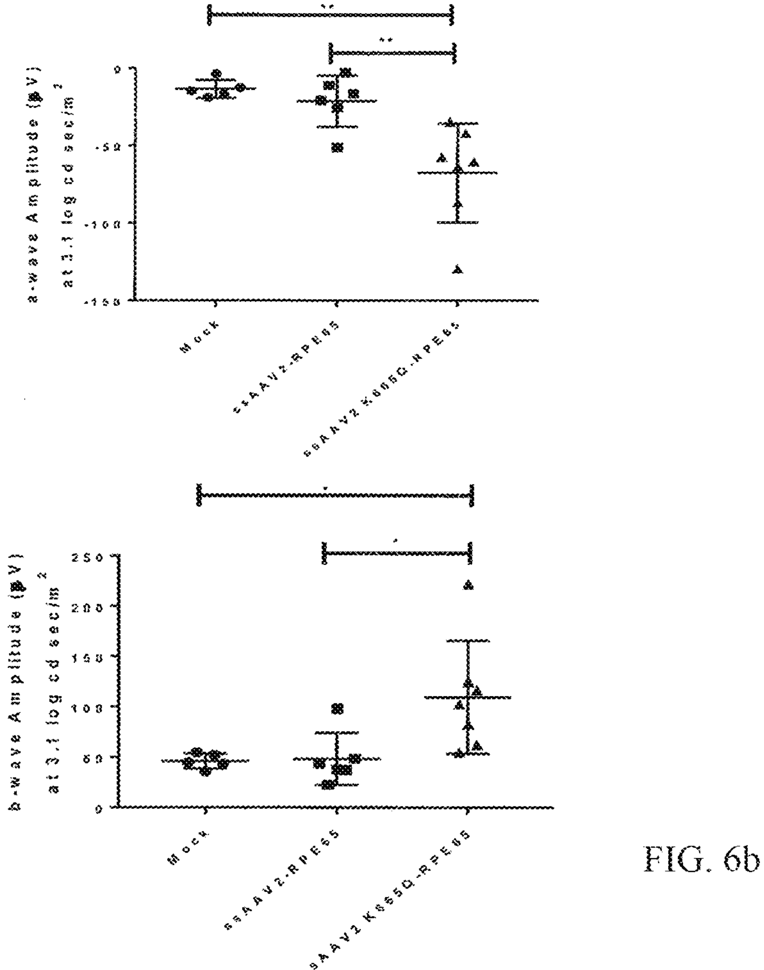

To further evaluate the therapeutic efficiency of AAV2-K665Q vectors for ocular gene therapy, we administered AAV2 wild type and K665Q expressing human retinal pigmental epithelium gene encoding 65 kda protein (RPE65) in groups of rd12 mice. Approximately, 1-2 μl of vectors containing $7\times10^8$ vgs were administered by subretinal route into the eyes of rd12 mice. The phenotypic rescue was measured by electroretinography (ERG) analysis 6 weeks after vector administration. Representative ERG waveforms are shown in FIG. 6*a*. The A-wave amplitude for K665Q vector administered mice was significantly elevated to −67.66±12.04 μV in comparison to eyes that received AAV2 wild type vectors (−25.07±12.69 μV) and mock injected animals (−13.4±2.0 μV) (FIG. 6*b*). The B-wave amplitude for AAV2 K665Q administered and AAV2 wild type administered eyes were 109.3±56.17 μV and 55.07±15.12 μV, respectively (FIG. 6*b*). This highlights that ocular gene therapy with AAV2 K665Q-RPE65 vectors has a therapeutic A-wave amplitude response (P<0.01) and B-wave response (P<0.05) when compared to rd12 mice that received wild type AAV2 vectors.

The present invention identifies that AAV2 infection of HeLa cells upregulates crucial arms (APPBP1, UBA3, UBC12) of Neddylation signaling pathway. Conversely, the inhibition of Neddylation by a small molecular inhibitor, MLN4924 improved AAV transduction by 50%. These data suggest that cellular Neddylation status could regulate AAV vector transduction. These data are similar to previous studies [Yan Z, Zak R Luxton G W G, et al., Ubiquitination of both Adeno-Associated Virus Type 2 and 5 Capsid Proteins Affects the Transduction Efficiency of Recombinant Vectors. J Viral 2002; Zhong L. Zhao W, Wu J. et al., A dual role of EGFR protein tyrosine kinase signaling in ubiquitination of AAV2 capsids and viral second-strand DNA synthesis, Mol Ther 2007; and Zhong L, Li B. Jayandharan G. et al., Tyrosine-phosphorylation of AAV2 vectors and its consequences on viral intracellular trafficking and transgene expression, Virology Elsevier Inc. 2008] that established the role of ubiquitination in AAV2 life cycle. The present invention identifies that the infection of AAV triggers intracellular Neddylation machinery and further leads to interdependent activation of the E3 (CRLs) of ubiquitin pathway and the ubiquitination of the viral capsid. The interdependency of ubiquitination and Neddylation has been shown in the case of p53, which was either ubiquitinated and Neddylated by the same E3 ligase (MDM2) under different cellular conditions. Further, the substrate modification at lysine residue by either ubiquitination or Neddylation is also known to result in various effector functions [Enchev R I, et al., Protein neddylation: beyond cullin—RING ligases. Nat Publ Gr Nature Publishing Group 2015].

Based on experiments conducted, the present invention provides that the NEDD8 inhibitor improves AAV2 transduction presents a possibility of co-administration of Neddylation inhibitors during AAV mediated gene transfer to improve its transduction. However. Neddylation is a crucial factor for maintenance of normal cellular physiology and thus this approach is likely to lead to severe side effects. Therefore, the present process provides for modifying the AAV2 capsid residues that are potentially Neddylated and as determined by prediction algorithms [Yavuz A S, Osman U., Prediction of neddylation sites from protein sequences and sequence-derived properties, 2015]. The data generated by the aforementioned experiments shows that the abolishment of Neddylation sites on the AAV2 capsid increases its transduction efficiency by 46% to 165% in multiple cell lines. To understand, if this increase is due to an improved uptake of the mutant vectors by the HeLa cells, the viral entry assay was performed. The entry profile of K665Q mutant was similar to WT-AAV2 (FIG. 7) 3 hours after transduction with the vectors. This suggests that intracellular mechanisms were more likely to lead to enhanced transduction seen with the K665Q mutant. The present invention also assesses the neutralization of mutant vectors by intravenous immunoglobulins (IVIG), but none of the mutant vectors developed had an immune escape potential (FIG. 7). In vivo, the mutant vector (K665Q) showed a significantly higher transduction of retinal layer in comparison to WT-AAV2 vector 2 or 8 weeks after intravitreal administration. This data is encouraging as intravitreal injections are simple as compared to subretinal injections that require major surgical vitrectomy. Further in contrast, subretinal injections can cause temporary bleb in the retina which can cause local inflammation and requires precise surgical intervention that increases the complexity of ocular gene delivery as opposed to the present process.

The claim of improved ocular transduction with K665Q mutant of AAV2 by the present invention is significant in light of the application of the Neddylation site modified AAV vector in performing ocular gene therapy. The data from patients treated with an AAV based gene therapy protocol suggest a significant loss in vision owing to low-level expression of RPE65 in addition to undefined immune response to AAV vectors. Nonetheless, ~30-70% of humans are seropositive to AAV2, which is likely a major barrier for its administration [as provided by Monteilhet V, Veron P, Leborgne C. et al. Prevalence of Serum IgG and Neutralizing Factors and in the Healthy Population: Implications for Gene Therapy Using AAV Vectors. Hum Gene Ther 2010 and Calcedo R, Vandenberghe L H, Gao G, et al. Worldwide Epidemiology of Neutralizing Antibodies to Adeno-Associated Viruses. J Infect Dis 2009]. Therefore, for an AAV2 vector to be widely therapeutic in such settings, improving the efficiency of transgene delivery and imparting immune escape function to the vector are crucial. The present invention provides for a vector with improved transduction, with a less invasive intra-vitreal gene transfer route. However, further studies are needed to understand the mechanistic basis of how the Neddylation site K665Q modification leads to improved gene transfer and if it has any impact on cellular immune response in vivo.

Neddylation Site Modified AAV2 Vectors Improve Circulating Levels of Coagulation Factor IX in Hemophilia B Mice In anticipation of testing the in vivo efficacy of AAV mutant vectors developed here, we first pre-screened the scAAV2 wildtype and K665Q vectors expressing human coagulation factor IX (h.FIX) in Huh7 cells. As can be seen in FIG. 9*a*, the K665Q vectors demonstrated a 3.9-fold increase in h.FIX transcript levels. We then investigated the therapeutic potential of K665Q vectors in a pre-clinical model of hemophilia B. Groups of hemophilia B mice (n=5 mice per group), were mock (PBS)-injected or injected AAV2 wild-type, K665Q mutant vectors expressing h.FIX at a dose of $5\times10^{10}$ vgs per animal. The h.FIX antigen levels were assessed 5 and 8 weeks, post vector administration by h.FIX specific ELISA. At the five weeks' time point, the mean h.FIX levels in animals that received the mutant K665Q was 104.5%±20.9, whereas in animals that received the wild type vectors the h.FIX levels were of 49.83%±36.66. After 8 weeks, h.FIX levels were near normal levels in animals that received mutant AAV2 [108.8%±32.18 (K665Q)] when compared to wild type AAV2 vector injected animals [52.92%±37.54 of (FIG. 9*b*)]. These data were further corroborated by immunostaining, that showed a higher h.FIX expression in liver sections of K665Q mutant administered mice when compared to AAV2 administered mice (FIG. 10). These findings highlight that a single injection of Neddylation mutant AAV2-h.FIX vectors can generate physiological levels of h.FIX and further confirms their therapeutic potential for hepatic gene therapy of hemophilia B.

Neddylation Mutant Vectors are not Immunogenic in Comparison to Wildtype AAV2 Vectors In this set of studies, the immune profile of the mutant AAV2-h.FIX vectors were characterized 9 weeks after hepatic gene transfer in hemophilia B mice. As can be seen in FIG. 11*a-d*, it was not observed a significant increase in the subpopulation of T cells including T-helper cells (14.67%±2.75 (AAV2) versus 14.05%±2.91 (K665Q); cytotoxic T cells (14.59%±2.07 (AAV2) versus 14.68%±3.62 (K665Q); or regulatory T cells (1.70%±0.38 (AAV2) versus 1.35%±0.34 (K665Q) between the mutant and wildtype AAV2 vector administered hemophilia B animals. A similar data was obtained when the B-cells were enumerated (FIG. 11*d*).

Furthermore, splenocytes were harvested from the mock treated and AAV2 treated mice and the capsid specific CD8+ T cell-based response was evaluated by the IFN-γ ELISPOT assay. Our data shown in FIG. 12, demonstrates that the IFN-γ response from splenocytes in animals that had gene transfer was at basal levels and was not significantly different between splenocytes of mice that received wildtype AAV2 or mutant AAV2 vectors. This data suggests that in murine models of hemophilia B, the host T-cell response against AAV2 vectors is negligible after a single, low dose of AAV2 vectors as demonstrated by Manno C S, Arruda V R, Pierce G F, et al. (Successful transduction of liver in hemophilia by AAV-Factor IX and limitations imposed by the host immune response. Nat Med 2006; 12(3):342-47.).

Figure 11:
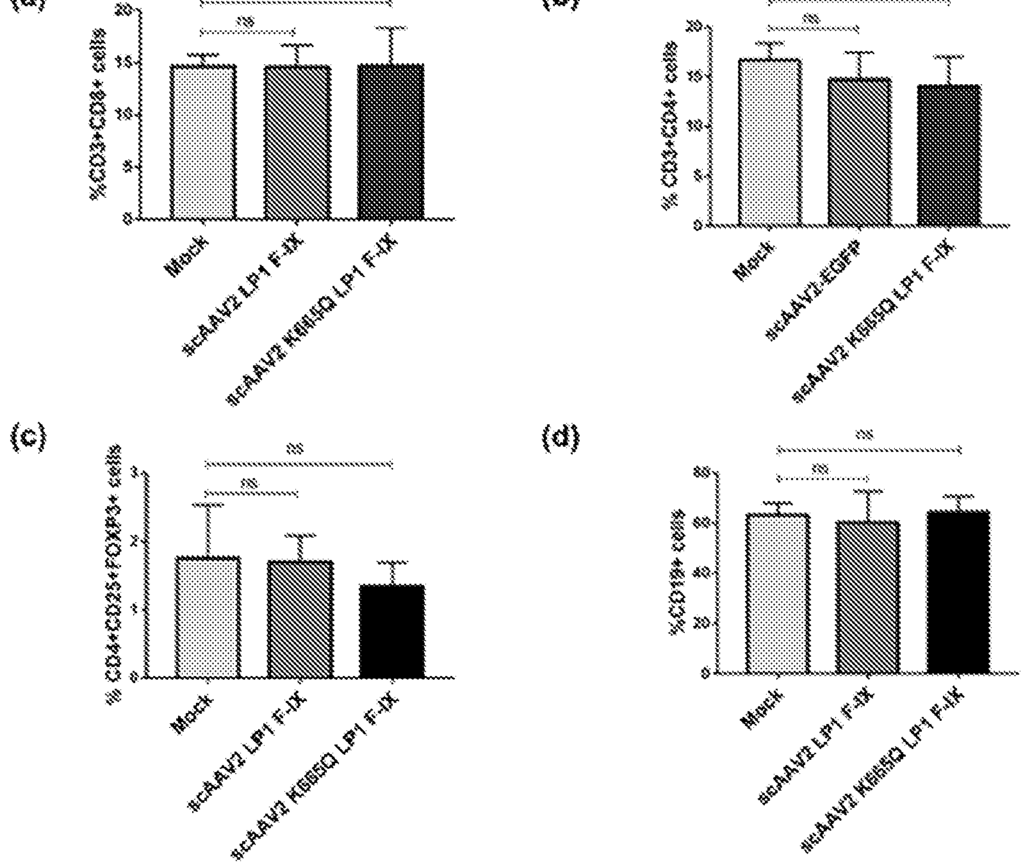
Figure 12:
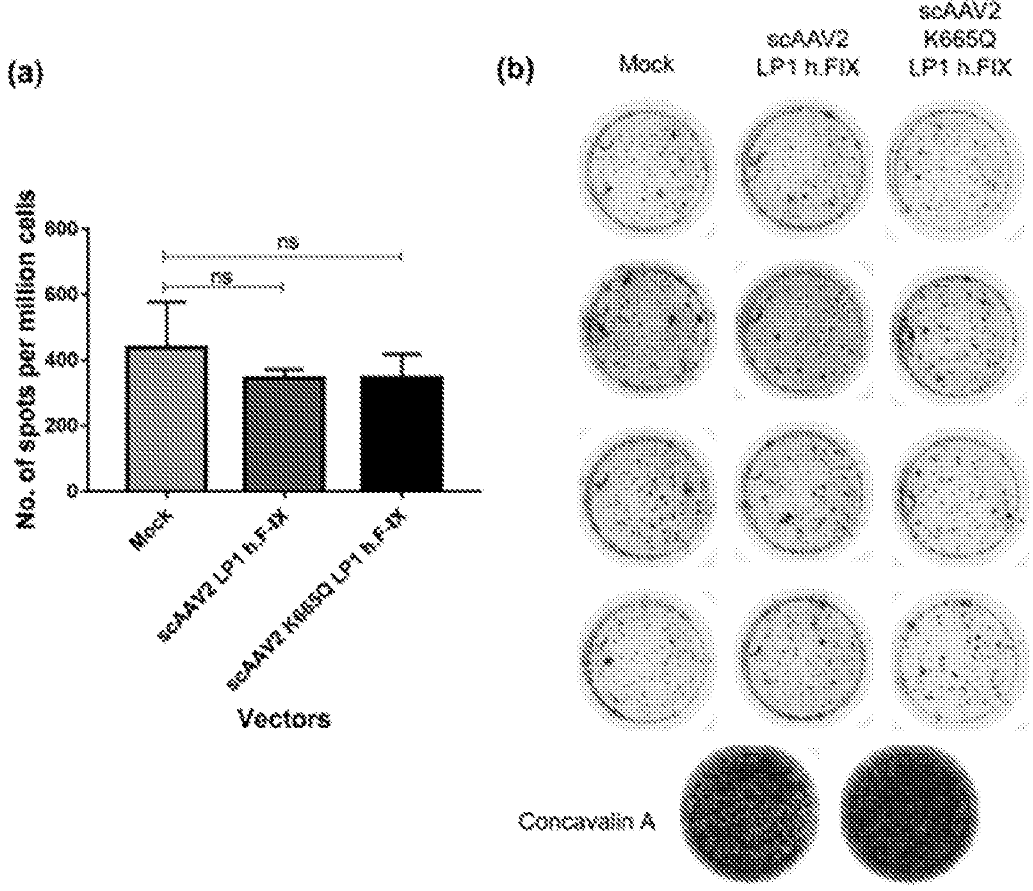

To further understand if these modified vectors have therapeutic potential during systemic gene therapy, hepatic gene transfer of AAV2-K665Q vectors packaged with human coagulation h.FIX in a murine model of hemophilia B was performed. Mutant vectors demonstrated a significant increase in h.FIX levels in hemophilia B mice. Two months after gene transfer, the h.FIX levels in AAV2-K665Q [median-100.1% (80.47%-161.9%)] remained significantly higher when compared to animals that were administered with wild type AAV2 vector [median-38.02% (20.7%-115.9%)]. Additionally, these mutant AAV2 vectors had an immune profile similar to wildtype AAV2 vectors (FIGS. 11 and 12). Taken together, these findings suggest it is possible to achieve physiological levels of h.FIX expression at very low doses of AAV2-K665Q vectors, without activating the cellular immune response in vivo.

Taken together, present invention highlights the therapeutic potential of the Neddylation site modified AAV vectors for ocular and hepatic gene therapy. The scope of use of the Neddylation site modified AAV vectors is immense in the therapy.

While specific language has been used to describe the invention, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Also, those acts that are not dependent on other acts may be performed in parallel with the other acts. The scope of embodiments is by no means limited by these specific examples.

The invention claimed is:

1. A process for producing a plurality of Neddylation site modified AAV2 vectors, comprising:

predicting a plurality of Neddylation sites on an AAV2 VP1 capsid protein sequence based on confidence targets; and producing the plurality of Neddylation site modified AAV2 vectors based on predicted plurality of neddylation sites on the AAV2 VP1 capsid protein sequence, wherein the producing of the plurality of Neddylation site modified AAV2 vectors comprises selecting the predicted plurality of neddylation sites, having a score of more than 0.3, on AAV2 VP1 capsid protein sequence for site-directed mutagenesis, wherein the neddylation sites are selected; and mutating the selected Neddylation sites from Lysine (K) Glutamine (Q) residues produce a plurality of Neddylation site modified AAV2 vectors.

2. The process as claimed in claim 1, wherein the plurality of Neddylation sites on AAV2 VP1 capsid protein sequence are predicted in-silico.

3. The process as claimed in claim 1, wherein mutating the selected Neddylation sites is performed using a set of primers designed for abolishment of the selected Neddylation sites from Lysine (K) to Glutamine (Q), where the set of primers has been set forth in SEQ ID Nos. 1 to 10.

4. The process as claimed in claim 1, wherein the plurality of Neddylation site modified AAV2 vectors possess at least 60% increase in gene expression, with respect to wild type, after hepatic and ocular gene transfer.

5. The process as claimed in claim 1, further comprising purifying the produced plurality of Neddylation site modified AAV2 vectors; and packaging the purified plurality of Neddylation site modified AAV2 vectors.

6. The process as claimed in claim 1, further comprises evaluating the plurality of Neddylation site modified AAV2 vectors by intraocular or hepatic gene transfer in order to demonstrate improved retinal transduction or hepatic transduction in murine models of retinal degeneration or hemophilia in vivo.

7. A plurality of Neddylation site modified AAV2 vectors produced by the process of claim 1.

* * * * *